(12) United States Patent
Ding et al.

(10) Patent No.: US 10,589,215 B2
(45) Date of Patent: Mar. 17, 2020

(54) PRODUCTION OF BIOMETHANE USING MULTIPLE TYPES OF MEMBRANE

(71) Applicant: Air Liquide Advanced Technologies, U.S. LLC, Houston, TX (US)

(72) Inventors: Yong Ding, Waban, MA (US); Michael J. Mitariten, Pittstown, NJ (US)

(73) Assignee: Air Liquide Advanced Technologies U.S. LLC, Houston, TX (US)

( * ) Notice: Subject to any disclaimer, the term of this patent is extended or adjusted under 35 U.S.C. 154(b) by 118 days.

(21) Appl. No.: 15/711,571

(22) Filed: Sep. 21, 2017

(65) Prior Publication Data
US 2019/0030482 A1    Jan. 31, 2019

(51) Int. Cl.

| | | |
|---|---|---|
| *B01D 53/22* | (2006.01) | |
| *B01D 53/26* | (2006.01) | |
| *B01D 69/12* | (2006.01) | |
| *B01D 71/80* | (2006.01) | |
| *C07C 7/144* | (2006.01) | |
| *C07C 7/00* | (2006.01) | |
| *C10L 3/10* | (2006.01) | |
| *B01D 71/56* | (2006.01) | |
| *B01D 71/52* | (2006.01) | |

(52) U.S. Cl.
CPC ......... *B01D 53/226* (2013.01); *B01D 53/228* (2013.01); *B01D 53/265* (2013.01); *B01D 53/268* (2013.01); *B01D 69/12* (2013.01); *B01D 71/80* (2013.01); *C07C 7/005* (2013.01); *C07C 7/144* (2013.01); *C10L 3/103* (2013.01); *C10L 3/104* (2013.01); *C10L 3/106* (2013.01); *B01D 71/52* (2013.01); *B01D 71/56* (2013.01); *B01D 2319/022* (2013.01); *C10L 2290/548* (2013.01)

(58) Field of Classification Search
None
See application file for complete search history.

(56) References Cited

U.S. PATENT DOCUMENTS

| 4,963,165 A | 10/1990 | Blume et al. |
|---|---|---|
| 5,401,300 A | 3/1995 | Lokhandwala et al. |
| (Continued) | | |

FOREIGN PATENT DOCUMENTS

| WO | WO 2015/123257 | 8/2015 |
|---|---|---|
| WO | WO 2016/107786 | 7/2016 |

OTHER PUBLICATIONS

Scholz et al. Transforming biogas into biomethane using membrane technology, 2013, pp. 199-212.*

(Continued)

*Primary Examiner* — Tam M Nguyen
(74) *Attorney, Agent, or Firm* — Christopher J. Cronin

(57) ABSTRACT

The invention relates to a process for recovering methane from digester biogas or landfill gas. More specifically, the invention pertains to a method for producing biomethane that removes impurities from a compressed digester biogas with staged membrane modules of at least two different types, to produce a biomethane having at least 94% $CH_4$, below 3% of $CO_2$, and below 4 ppm of $H_2S$.

18 Claims, 3 Drawing Sheets

(56) References Cited

U.S. PATENT DOCUMENTS

| | | | |
|---|---|---|---|
| 5,669,958 A | 9/1997 | Baker et al. | |
| 5,776,990 A | 7/1998 | Hedrick et al. | |
| 6,053,965 A | 4/2000 | Lokhandwala | |
| 6,860,920 B2 | 3/2005 | Simmons | |
| 7,025,803 B2 | 4/2006 | Wascheck et al. | |
| 8,999,038 B2 | 4/2015 | Ungerank et al. | |
| 2007/0006732 A1 | 1/2007 | Mitariten | |
| 2008/0034789 A1 | 2/2008 | Fieler et al. | |
| 2009/0156875 A1* | 6/2009 | Tomioka | B01D 3/101 585/802 |
| 2010/0111784 A1 | 5/2010 | Mak et al. | |
| 2010/0186586 A1 | 7/2010 | Chinn et al. | |
| 2011/0094378 A1* | 4/2011 | Mitariten | B01D 53/229 95/50 |
| 2012/0157743 A1* | 6/2012 | Liu | B01D 53/22 585/818 |
| 2012/0322119 A1* | 12/2012 | Liu | B01D 53/228 435/161 |
| 2012/0323059 A1* | 12/2012 | Liu | C07C 7/144 585/818 |
| 2013/0111949 A1 | 5/2013 | Gearhart et al. | |
| 2013/0255490 A1 | 10/2013 | Matteucci et al. | |
| 2014/0251897 A1 | 9/2014 | Livingston et al. | |
| 2014/0345880 A1 | 11/2014 | Enis et al. | |
| 2015/0053079 A1 | 2/2015 | Koros et al. | |
| 2017/0157555 A1* | 6/2017 | Karode | B01D 53/225 |
| 2017/0157556 A1 | 6/2017 | Karode et al. | |
| 2017/0157557 A1 | 6/2017 | Ding et al. | |
| 2018/0223205 A1* | 8/2018 | Mitariten | B01D 53/229 |
| 2019/0224617 A1* | 7/2019 | Mitariten | C07C 7/005 |

OTHER PUBLICATIONS

Rabiee, et al., "Gas transport properties of reverse-selective poly (ether-b-amide6)/[Emim][BF4] gel membranes for CO2/light gases separation," Journal of Membrane Science 476 (2015) 286-302.

Nunes, et al, "Dense hydrophilic composite membranes for ultrafiltration," Journal of Membrane Science 106 (1995)49-58; p. 50, section 2.

Yampolskii, et al, "Membrane Gas Separation," Wiley, 2010; p. 230, paragraphs 2-3; p. 231, paragraph 3; p. 231, figure 12,1(b).

Zhai, et al., "Technical and Economic Assessment of Membrane-based Systems for Capturing CO2 from Coal-fired Power Plants," Presentation to the 2011 AlchE Spring Meeting, Chicago, Il.

International Search Report and Written Opinion for PCT/US2018/051645, dated Dec. 6, 2018.

Scholz, et al., "Transforming Biogas into Biomethane using Membrane Technology," Renewable and Sustainable Energy Reviews, 2013, vol. 17, pp. 199-212.

Bernardo, et al., "Membrane Gas Separation: A Review/State of the Art," Ind. Eng Chem. Res. 2009, vol. 48, pp. 4638-4663.

Molino, et al., "Biogas Upgrading via Membrane Process: Modelling of Pilot Plant Scale and the Grid Injection," Fuel, 2013, vol. 107, pp. 585-592.

Hao, et al., "Upgrading Low-Quality Natural Gas with H2S and CO2-Selective Polymer Membranes Part II, Process Design, Economics, and Sensitivity Study of Membrane Stages with Recycle Streams," Journal of Membrane Science, 2008, vol. 320, pp. 108-122.

* cited by examiner

PRODUCTION OF BIOMETHANE USING MULTIPLE TYPES OF MEMBRANE

FIELD OF THE INVENTION

The invention pertains to biomethane production by processing compressed biogas through multiple membrane stages, wherein at least two membrane stages have different membrane types.

BACKGROUND OF THE INVENTION

Biogas typically refers to a mixture of different gases produced from the breakdown of organic matter without oxygen in an anaerobic digestion process. Biogas can be produced from raw materials such as agricultural waste, manure, municipal waste, plant material, sewage, green waste or food waste. Biogas typically comprises as the main components 50-70% of methane ("$CH_4$") and 20 to 50% carbon dioxide ("$CO_2$"), with lower levels of other components such as $N_2$ and $O_2$, up to 5,000 ppm or more of hydrogen sulfide ("$H_2S$"), siloxanes, up to 1,000-2,000 ppm of volatile organic compounds ("VOC's"), and is saturated with water. Biogas also includes landfill gas ("LFG"), which is derived from solid waste landfills that decompose to the organic waste with time, via microbe digestion of the variety of organic waste to produce methane and $CO_2$. In either case, biogas includes high concentrations of methane and carbon dioxide, water vapor, and lesser concentrations of VOC's and other contaminants.

Specifically, digester biogas ("digester gas") or landfill gas is a type of renewable energy. Methane or natural gas is a combustible fuel for supplying energy, and also as a raw material in many industrial significant processes. Thus, it is very desirable from an economic and environmental viewpoint to capture the methane from digester or landfill exhaust gas, especially since biogas is a renewable source and not a fossil fuel.

If digester and landfill exhaust gas is not recovered, the methane that escapes into ambient air becomes a source of air pollution. Accordingly, it is further desirable to prevent the methane emissions produced from the anaerobic digestion, for environmental protection purposes. Traditionally, digester or landfill exhaust gas has been burnt in an open flame incinerator such as a flare stack, to prevent the gas from escaping to the environment. This burning process is inefficient, and consequently, a large fraction of the methane and other obnoxious contaminants in the exhaust gas survive to pollute the ambient air. Further when combusted $CO_2$, a potent greenhouse gas, is emitted. Also, common flare stack operations are a waste of the useful energy held by the methane in the exhaust gas.

Other conventional methods for recovering methane from digester and landfill exhaust gas, and other sources of crude natural gas have developed. These methods include gas separation processes in which the useful methane is separated from other components of the source gas. Favored conventional gas separation processes typically utilize adsorption-regeneration technology, in which the crude gas is processed by an adsorbent material that passes selected components of the crude and rejects others. For example, pressure swing adsorption ("PSA") or Thermal Swing Adsorption ("TSA") technologies involve selectively adsorbing contaminants of crude gas onto adsorbent particles, and allowing the so-called sweetened gas to pass through the PSA/TSA units.

Unfortunately, the adsorbent particles in the PSA/TSA units ultimately become saturated with the contaminants, and lose their abilities to adsorb beyond a maximum amount. Therefore, before more contaminants can be removed from the crude, the adsorbent particles must be regenerated. The regeneration process normally involves exposing the saturated particles to high temperatures and/or low pressures, and regeneration with fluids that have low concentrations of the contaminants to promote desorption of the contaminants from the particles. For example, TSA requires a supply of heat energy to heat the regeneration gas and PSA requires a supply of clean, usually low pressure gas. Additionally, the adsorption-regeneration technology also requires support facilities for removal of water vapor, and pre-conditioning the crude gas, e.g., by compressing it to high pressure. Thus, it is very costly in financial and energy consumption aspects to operate conventional adsorption-regeneration technologies, to recover useful methane from digester and landfill exhaust gas.

On the contrary, membrane systems are versatile and are known to process a wide range of feed compositions and separations. With a very compact footprint and low weight, these membrane systems are well suited for offshore applications, remote locations, or for smaller flow rates. Recent developments in dew point control include membrane designs that operate in condensing mode, as well as membranes that allow for the simultaneous removal of water and heavier hydrocarbons from natural gas.

Membranes have been used for biogas treatment. Typical membrane processes involve first removal of $H_2S$ by a sulfur removal unit, a further pretreatment by refrigeration and adsorption processes to remove water and VOCs, then followed by a two-stage membrane process that is dedicated to $CO_2$ removal, and further recycling/processing of the permeate from the second separation stage of membrane. U.S. Pat. No. 8,999,038 and WO 2016/107786, both assigned to Evonik Fibres GMBH, disclose a three-stage membrane process for $CO_2$ removal using membranes with $CO_2/CH_4$ selectivity higher than 50. These processes do not simultaneously remove $H_2S$ and $CO_2$ while achieving high methane recovery (≥94%).

It is also well documented that glassy polymers, such as polyimide, polysulfone, polybenzimidazole, etc., exhibit exceptional high intrinsic $CO_2$/methane selectivity. However, the selectivity and permeance of the membranes prepared from those materials often quickly decrease, once they are used for methane gas extraction in the presence of VOC's and other biogas impurities. This loss of membrane performance is caused by condensation and coating of the VOC's and siloxanes on the membrane surface or due to adsorption of the heavy components in the membrane fiber. The conventional solution for this problem is to use a system including a regenerable adsorbent bed, followed by a carbon trap for removing the water, siloxanes and VOC's upstream of the membrane used for $CO_2$ removal. Although these pretreatment systems can effectively remove VOC's and other components from the biogas stream, the cost of the pretreatment and/or frequent membrane replacement can be prohibitive. Indeed, the cost of the pretreatment system can be as high as 50% of the total system cost (pretreatment plus membrane).

Further, the product gas produced from digester gas and landfill gas must meet safety criteria to be injected into the utility pipeline. In particular, a common industry standard aims to comply with SoCalGas® Rule 30 and PG&E Rule 21, which set forth the standards for utility methane gas injection in large portions of California. Specifically, according to Rule 30, the methane gas to be delivered should have:

a) Heating Value: The minimum heating value of nine hundred and ninety (990) Btu (gross) per standard cubic foot on a dry basis, a maximum heating value of one thousand one hundred fifty (1150) Btu (gross) per standard cubic foot on a dry basis.

b) Moisture Content or Water Content: For gas delivered at or below a pressure of eight hundred (800) psig, the gas shall have a water content not in excess of seven (7) pounds per million standard cubic feet. For gas delivered at a pressure exceeding of eight hundred (800) psig, the gas shall have a water dew point not exceeding 20° F. at delivery pressure.

c) Hydrogen Sulfide: The gas shall not contain more than twenty-five hundredths (0.25) of one (1) grain of hydrogen sulfide, measured as hydrogen sulfide, per one hundred (100) standard cubic feet (4 ppm). The gas shall not contain any entrained hydrogen sulfide treatment chemical (solvent) or its by-products in the gas stream.

d) Mercaptan Sulfur: The gas shall not contain more than three tenths (0.3) grains of mercaptan sulfur, measured as sulfur, per hundred standard cubic feet (5 ppm).

e) Total Sulfur: The gas shall not contain more than seventy-five hundredths (0.75) of a grain of total sulfur compounds, measured as a sulfur, per one hundred (100) standard cubic feet (12.6 ppm). This includes COS and $CS_2$, hydrogen sulfide, mercaptans and mono, di and poly sulfides.

f) Carbon Dioxide: The gas shall not have a total carbon dioxide content in excess of three percent (3%) by volume.

g) Oxygen: The gas shall not have an oxygen content in excess of two-tenths of one percent (0.2%) by volume, and customer will make every reasonable effort to keep the gas free of oxygen.

h) Inerts: The gas shall not contain in excess of four percent (4%) total inerts (the total combined carbon dioxide, nitrogen, oxygen and any other inert compound) by volume.

i) Hydrocarbons: For gas delivered at a pressure of 800 psig or less, the gas hydrocarbon dew point is not to exceed 45° F. at 400 psig, or at the delivery pressure, if the delivery pressure is below 400 psig. For gas delivered at a pressure higher than 800 psig, the gas hydrocarbon dew point is not to exceed 20° F., measured at a pressure of 400 psig.

These gas constituent limits restrict the concentration of gas impurities to protect pipeline integrity, and ensure safe and proper combustion in end-user equipment. In particular, the hydrocarbon dew point requirement and the reduction of heavy hydrocarbons prevent unsafe formation of a liquid phase during transport. The hydrocarbon dew point is sensitive to small quantities of $C_{6+}$ and VOC components. As little as 450 ppm of $C_8$ hydrocarbon added to a lean gas can give it a cricondentherm of 50° F.

There are other known attempts to produce purified methane from biogas or natural gas.

U.S. Pat. No. 7,025,803 to Wascheck, et al. recovers high concentrations of methane from crude natural gas and solid waste landfill exhaust gas, using a sequential combination of a pressure swing adsorber unit operation to remove volatile organic compounds from the crude feed gas mixture, followed by an activated carbon bed, and a membrane separation unit operation. However, the system in '803 is relatively costly for some system operators and does not satisfactorily handle relatively high levels of $H_2S$. Therefore, a separate $H_2S$ removal system (such as SulfaTreat or other treatment methods) may be required for raw biogas containing relatively high $H_2S$ levels, and an activated carbon bed may be required for reaching a desirably low VOCs level.

U.S. Publication No. 2017/0157555 to Karode, et al. teaches purification of natural gas by removing $C_{3+}$ hydrocarbons and $CO_2$ in respective first and second gas separation membrane stages to yield a conditioned gas that is lower in $C_{3+}$ hydrocarbons and $CO_2$, in comparison to the unconditioned natural gas. The '555 publication is not concerned with producing biomethane, or removing VOC's and siloxane from biogas. Further, product gas from natural gas sweetening typically contains a mixture of methane, ethane, and natural gas liquids.

PEEK membranes previously marketed by Porogen (now Air Liquide) remove sulfur gas ($H_2S$), but have a relative low selectivity for $CO_2$ over $CH_4$.

Therefore, there remains a need for processing biogas or landfill gas in a membrane gas separation system, to remove VOC's, siloxane, $H_2S$, $CO_2$ and other impurities, as well as to achieve dehydration and dew point control simultaneously at a low cost, in order to produce biomethane suitable for utility pipeline delivery within minimal pretreatment.

SUMMARY

There is disclosed a method for producing biomethane from biogas, comprising the following steps. A stream of biogas is compressed in a main compressor and the compressed stream is passed to a first separation stage containing at least one polymeric gas separation membrane (having a selectivity for $H_2S$ over $CH_4$) permeating a first low quality gas having less than 20% methane and impurities such as $H_2S$, water, siloxane, $CO_2$, and VOC's. The retentate or a first gas mixture, having at least 60% methane from the first separation stage is then passed to a second separation stage containing at least one polymeric gas separation membrane having a selectivity for $CO_2$ and $H_2S$ over $CH_4$, to produce biomethane having at least 94% methane, $CO_2$ below 3%, below 100 ppm of $H_2S$, below 100 ppm of VOC's, siloxane below 100 ppm and below 7 lbs. per million standard cubic feet or 0.5 wt. % of $H_2O$. The second separation stage permeates impurities and less than 70% methane. The membranes from the first separation stage are substantially different from the membranes in the second separation stage. The permeate from the second membrane is then recycled back to the main compressor. Specifically, the second permeate gas mixture is fed to the suction inlet, of the main compressor, or combined with the biogas feed upstream of the suction inlet so that the second gas mixture is compressed along with the biogas feed.

There is also provided a system for producing biomethane, comprising a source of biogas feed; a compressor that compresses the feed; a first separation stage that contains at least one polymeric gas separation membrane in fluid communication with the compressed feed, to process the compressed feed, wherein the first separation stage has a selectivity of $H_2S$ over $CH_4$, in the value of at least 10, preferably of at least 30, expressed in ratio of permeance, a second separation stage that contains at least one polymeric gas separation membrane in fluid communication with the first separation stage, process a retentate from the first separation stage to produce biomethane, wherein the second separation stage has a selectivity of $CO_2$ over $CH_4$, in the value of at least 20, preferably of at least 35, expressed as ratio of permeance; an inlet for recycling a permeate from the second separation stage back to the compressor inlet, thereby commingling the biogas feed with the second stage permeate stream as a mixed gas feed to the compressor, so that the compressor compresses and discharges the compressed feed to the first separation stage of membrane, wherein the system is free of any regenerable adsorbent beds or pressure swing adsorption systems.

This novel method and system simultaneously removes water, hydrogen sulfide, carbon dioxide and VOC's at the same time while exhibiting a methane recovery of at least 94%. The novel process excludes the use of regenerative adsorption systems.

The method and/or system may include one more of the following aspects:

The biogas feed contains 40-75% of methane ("$CH_4$"), and impurities of up to 10% nitrogen ("$N_2$"), up to 1% oxygen ("$O_2$"), 20-55% of carbon dioxide ("$CO_2$"), up to 5,000 ppm or more of hydrogen sulfide ("$H_2S$"), siloxanes, up to 1,000-2,000 ppm of VOCs and water.

The step of compressing a stream of biogas in a main compressor may include passing the compressed feed stream to a water removal apparatus to remove water, the water removal apparatus optionally being a condenser. The water is removed such that the compressed feed stream has a water content of less than 0.5 wt. %.

At least one gas separation membrane of the first separation stage is comprised of a porous polymeric substrate having at least one separation layer, wherein the substrate is selected from the group consisting of polyimides, poly sulfones, polyether ether ketones ("PEEK"), and mixtures thereof.

At least one gas separation membrane of the first separation stage is comprised of a porous polymeric substrate having at least one separation layer, wherein the substrate is polyether ether ketones ("PEEK").

At least one gas separation membrane of the first separation stage is comprised of a porous polymeric substrate having at least one separation layer, the separation layer being made of a copolymer or block polymer of the formula:

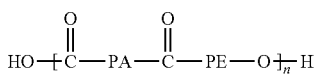

wherein PA is an aliphatic polyamide having 6 or 12 carbon atoms and PE is either poly(ethylene oxide) poly(tetramethylene oxide).

At least one gas separation membrane of the first separation stage is comprised of a porous polymeric substrate having at least one separation layer, the separation layer being made of a copolymer or block polymer made of repeating units of the following monomers:

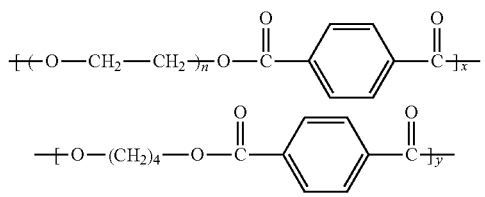

Alternatively, the separation layer is made of a copolymer or block polymer of tetramethylene oxide, and/or propylene oxide, or ethylene oxide.

Overall, at least one membrane of the first separation stage is in the form of flat films or a plurality of hollow fibers.

At least one gas separation membrane of the first separation stage has a selectivity for $H_2S$, VOC's, $CO_2$, siloxane and $H_2O$ over $CH_4$. The membrane has a selectivity of at least 4, preferably at least 6, and below 10 of $CO_2$ over $CH_4$. The membrane also has a selectivity of at least 10, preferably at least 30 for $H_2S$ over $CH_4$.

The gas separation membrane of the first separation stage also has a specific surface area of about 15-30 $m^2/g$, and a pore size of below 1 micrometer.

The stream of the first gas mixture has a pressure drop of less than 50 psi, preferably less than 30 psi, from the feed gas.

The first gas mixture produced from the first separation stage is comprised of at least 40% methane, at least 25% carbon dioxide, less than 1000 ppm of hydrogen sulfide, less than 100 ppm of VOC's and siloxane, and less than 0.05 wt. % of water.

The first low-quality permeate gas mixture produced from the first separation stage is comprised of about 15% of methane, up to 10,000 ppm of $H_2S$, up to 3 wt. % of water and 85% of $CO_2$.

The first low-quality permeate gas mixture produced from the first separation stage is comprised of methane, up to 10,000 ppm of $H_2S$, up to 0.3 wt. % of water and up to 85% of $CO_2$, the first low-quality permeate gas being deficient in methane compared to said compressed feed stream An output stream of the first low-quality gas mixture is flared.

Instead of sending the first gas mixture directly to the second separation state, the first gas mixture is sent to a $H_2S$ scavenger media, to produce a low-$H_2S$ output stream having less than 4 ppm of $H_2S$ from the scavenger media, and the low-$H_2S$ output stream is sent into the second separation stage.

The second separation stage contains at least one gas separation membrane that is made a material selected from the group consisting of cellulose acetate, a polysulfone, a polyimide, and mixtures thereof. Further, the second separation stage has a selectivity for $CO_2$ over $CH_4$, of at least 20, preferably of at least 35.

The product gas from the second separation stage is comprised of at least 94% methane, below 3% of $CO_2$, below 4 ppm of $H_2S$, below 100 ppm of VOC's, and below 0.01 wt. % of $H_2O$.

The second permeate gas mixture produced from the second separation stage is comprised of about 50% methane, at least 30% $CO_2$, below 1000 ppm of $H_2S$, below 1000 ppm of VOC's and below 0.05 wt. % of $H_2O$.

The second gas is sent to a $H_2S$ scavenger media, to produce a low-$H_2S$ product stream having less than 4 ppm of $H_2S$ from the media.

The permeate from the second stage is compressed in a second compressor, and the compressed permeate is fed to the first separation stage.

The system includes a water removal apparatus, such as a condenser, to remove water from the compressed biogas feed prior to feeding the feed into the first separation stage.

Each of the at least one gas separation membrane of the first separation stage exhibits a pressure drop between a pressure of the feed gas and a pressure of the retentate gas is less than 50 psi (3.45 bar), preferably less than 30 psi (2.07 bar).

At least one gas separation membrane of the first separation stage has a separation layer made of a copolymer or block polymer of the formula:

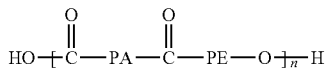

wherein PA is an aliphatic polyamide having 6 or 12 carbon atoms and PE is either poly(ethylene oxide) poly(tetramethylene oxide).

Alternatively, at least one membrane of the first separation stage has a separation layer made of repeating units of the following monomers:

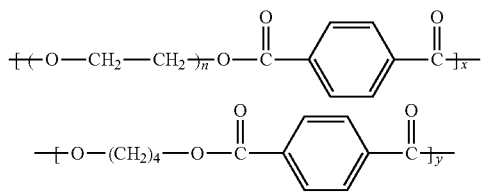

wherein said at least one membrane of said first separation stage is in the form of flat film or as a plurality of hollow fibers.

The separation layer of the first separation stage is supported by a support layer that is made of a polyimide, polysulfone, polyether ether ketone, or mixtures thereof. Preferably, the support layer is porous and is made of polyether ether ketone.

At least one membrane of the second separation stage is made of cellulose acetate, a polysulfone, a polyimide, or mixtures thereof.

The system may further include a $H_2S$ scavenger media located between and in fluid communication with the first separation stage and the second separation stage, to process a retentate from the first separation stage before the retentate is sent to the second separation stage.

The system may further include a $H_2S$ scavenger media located on the high pressure retentate of the second separation stage, and in fluid communication with the second separation stage, to process a retentate from the second separation stage to produce biomethane.

The system may further include a third separation stage of at least one polymeric gas separation membrane having a selectivity of $H_2S$, $H_2O$, and $CO_2$ over $CH_4$ in fluid communication with the first separation stage, for processing permeate from the first separation stage and producing as retentate an enriched methane stream.

At least one gas separation membrane of the third separation stage is made of any conventional rubbery or glassy gas separation material. Preferably, at least one membrane of the third stage is made of the same material as the gas separation membrane of the first of the second separation stage.

DETAILED DESCRIPTION OF THE INVENTION

Figure 1:
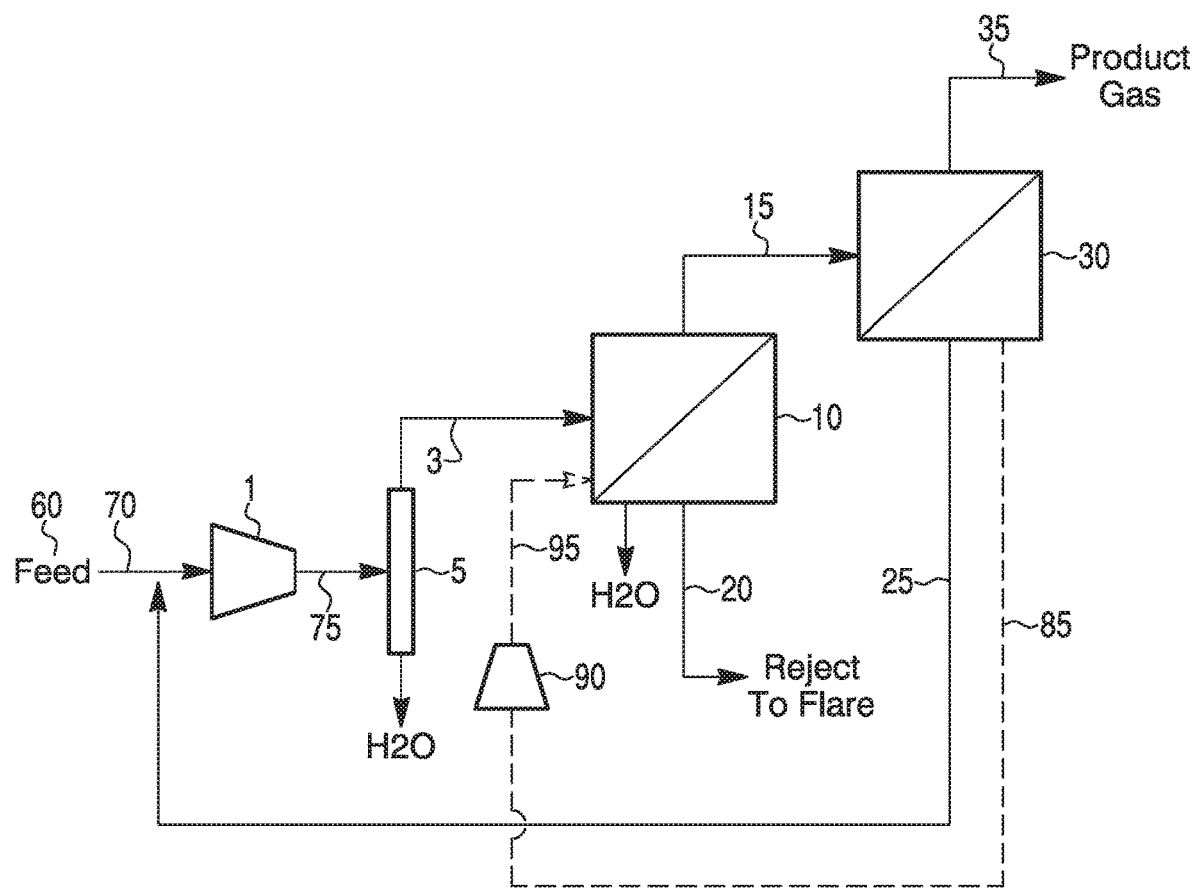
FIG. 1 illustrates a biomethane production by a two-stage membrane system.

There is a disclosed method for producing biomethane from biogas, comprising: compressing a stream of the biogas in a compressor; removing water from the compressed feed by cooling; and sending the dehydrated and compressed feed into a first separation stage containing at least one polymeric gas separation membrane having a selectivity of at least 10, preferably at least 30, for $H_2S$ over $CH_4$ to permeate a first low quality gas mixture having less than 20% methane and impurities such as $H_2S$, water, siloxane, $CO_2$, and VOC's, then passing the retentate or first gas mixture, having at least 60% methane from the first separation stage, to a second separation stage containing at least one polymeric gas separation membrane having a selectivity of at least 20, preferably at least 35, for $CO_2$ over $CH_4$ to produce a biomethane having at least 94% methane, below 3% of $CO_2$, below 100 ppm of $H_2S$, below 100 ppm of VOC's, below 100 ppm of siloxanes, and below 0.01 wt. % of water.

The membranes of the first separation stage are substantially different from the membranes in the second separation stage. More particularly, the polymeric membranes of the first separation stage may have a selectivity for $H_2S$ over $CH_4$ that is higher than the polymeric membranes of the second separation stage. More particularly, the polymeric membranes of the first separation stage may have a selectivity for $CO_2$ over $CH_4$ that is lower than the polymeric membranes of the second separation stage. More particularly, the polymeric membranes of the first separation stage may be rubbery membranes while the polymeric membranes of the second separation stage may be glassy membranes.

The permeate from the first separation stage is comprised of about 15% of methane, up to 10,000 ppm of $H_2S$, up to 3 wt. % of water and up to 85% of $CO_2$. The first permeate from the first separation stage is optionally fed into a third separation stage containing at least one polymeric gas separation membrane having a selectivity of at least 4, preferably at least 6, for $H_2S$ and $CO_2$ over $CH_4$, to concentrate the impurities within permeate to be vented or sent to an oxidizer for further treatment. The permeate from the second separation stage is comprised of about 50% to 80% methane, at least 20% $CO_2$, below 1,000 ppm of $H_2S$, below 1,000 ppm of VOC's and below 0.05 wt. % of $H_2O$. The permeate from the second separation stage and the retentate of the third separation stage may be recycled back to the main compressor, to be compressed and sent into the first separation stage to produce biomethane. Specifically, the second permeate gas mixture and the retentate from the third separation stage may be fed to the suction inlet of the main compressor, or combined with the biogas feed upstream of the suction inlet so that the combined stream is compressed along with the biogas feed.

The present invention excludes the use of regenerable adsorption systems, such as PSA, TSA, and VSA. Specifically, no regenerable adsorbent beds are used from an initial step of obtaining the biogas from the landfill (or digester) to a final step of obtaining the product biomethane gas. The exclusion of regenerable adsorbent beds reduces the cost, as well as eliminates the need for clean, low pressure gas and pre-conditioning facilities.

As used herein, the term "biogas" typically refers to a mixture of different gases produced from the breakdown of organic matter in the absence of oxygen in an anaerobic digestion process. Biogas can be produced from raw materials such as agricultural waste, manure, municipal waste, plant material, sewage, green waste or food waste.

Biogas typically comprises as the main components 50-70% of methane ($CH_4$) and 20 to 50% carbon dioxide ($CO_2$) with lower levels of other components such as $N_2$ and $O_2$, from up to 5,000 ppm or more of hydrogen sulfide ($H_2S$), up to 100 ppm of siloxanes, up to 1,000-2,000 ppm of volatile organic compounds (VOC's), and is saturated with water. Biogas also includes landfill gas (LFG), which is derived from solid waste landfills that decompose to organic waste with time, and microbe digestion of a variety of the organic waste to produce a methane and $CO_2$ with the wide variety of decomposition products above. In either case biogas includes high concentrations of methane and carbon dioxide, water vapor, and lesser concentrations of VOC's and other contaminants The composition of digester biogas (digester gas) or landfill gas varies depending upon the substrate composition, as well as the conditions within the anaerobic reactor (temperature, pH, and substrate concentration). The biogas or landfill gas of the present invention is entirely distinct from natural gas extracted from a subterranean or subsea geological formation, or that of a producing well. Specifically, the digester biogas or landfill gas of the present invention is essentially free (contains <100 ppm) of butane, ethane and propane, As used herein, the term "biomethane" refers to renewable natural gas (RNG) which is a pipeline-quality gas that is fully interchangeable with conventional natural gas and can be used in natural gas vehicles. Biomethane is essentially biogas (the gaseous product of the decomposition of organic matter) that has been processed to purity standards. Like conventional natural gas, biomethane can be used as a transportation fuel in the form of compressed natural gas (CNG) or liquefied natural gas (LNG). Biomethane qualifies as an advanced biofuel under the Renewable Fuel Standards. Typically, the biomethane produced according to the disclosed method and system meets the requirements of SoCal Gas® Rule 30 or PG&E Rule 21, predetermined requirements of the delivery pipeline or the predetermined requirements of the CNG station requirements and has at least 94%, preferably at least 97%, of methane, less than 3% $CO_2$, and less than 100 ppm $H_2S$ and VOC's.

Each component in a landfill gas or digester biogas stream, once contacted with polymeric membranes, has an intrinsic solubility in the polymers. Once dissolved in the polymeric matrix of the membranes, the components diffuse across the polymers from the high pressure side to the low pressure side at different rates. The permeability for a given gas component is thus a combination of solubility and diffusivity in a given polymer.

A given membrane may have selectivity for (i.e., is more permeable to), one gas over another gas. As used herein, the term "selectivity" refers to the ratio of two gas permeabilities in permeance, and the measure of the ability of a membrane to separate two gases. The selectivity (a), of $CO_2$ over $CH_4$ is calculated according to the below formula:

$$\alpha CO_2/CH_4 = \frac{P*CO_2}{P*CH_4}$$

wherein P is the permeance or the flow flux of the given gas component through membranes and is expressed as 1 gas permeation unit (gpu)=$10^{-6}$ $cm^3$(S.T.P)/(s·$cm^2$·cm Hg). It is derived from the following equation:

$$J = \frac{P^*}{\delta}(xP_f - yP_p) = \overrightarrow{P^*}(xP_f - yP_p)$$

Where:
J=the volume flux of a component ($cm^3$(S.T.P)/$cm^2$·S);
P*=membrane permeability that measures the ability of the membrane to permeate gas ($cm^3$(S.T.P)·cm/(s·$cm^2$·cm Hg));
$\overrightarrow{P*}$ =membrane permeance ($cm^3$(S.T.P.)/(s·$cm^2$·cm Hg))*;
δ=the membrane thickness (cm);
x=the mole fraction of the gas in the feed stream;
y=the mole fraction of the gas in the permeate stream;
$P_f$=the feed-side pressure (cm Hg);
$P_p$=the permeate-side pressure (cm Hg).

More details of the calculation of permeance can be found in "Technical and Economic Assessment of Membrane-based Systems for Capturing $CO_2$ from Coal-fired Power Plants" by Zhai, et al. in Presentation to the 2011 AIChE Spring Meeting, Chicago, Ill., which is incorporated by reference in its entirety.

Membranes of the First Separation Stage

The membranes of the first separation stage are selective for $H_2S$ over $CH_4$ and also for $CO_2$ over $CH_4$. Specifically, the membranes of the first separation stage have a selectivity of at least 10, preferably at least 30, for $H_2S$ over $CH_4$. These membranes also have a selectivity of at least 4, preferably at least 6, for $CO_2$ over $CH_4$.

While these membranes may be asymmetric membranes and comprised of a single polymeric material or polymeric blend, typically the membranes are comprised of a porous polymeric substrate having an additional separation layer or coating. While the polymeric material making up the substrate is not limited, it is typically selected from the group consisting of polyimides, polysulfones, and polyether ether ketones. More typically, it is made of polyether ether ketones (PEEK). The separation layer is supported by the substrate, which provides mechanical strength and may also separate gases. On the other hand, the separation layer is either wholly or primarily responsible for performing the desired separation. The membranes of the first separation stage typically known as "rubbery" membranes. The membranes of the first separation stage typically have a specific surface area above 20 $m^2$/g, preferably above 100 $m^2$/g, and a pore size of below 1 micrometer, preferably below 0.25 micrometer, and more preferably below 0.015 micrometer. The membranes of the first separation stage are in the form of a flat film, or as a plurality of hollow fibers.

In the context of composite hollow fibers, the separation layer may be configured as a sheath surrounding a core made of the support layer. In the case of hollow fibers, the fiber preferably possesses an outside diameter from about 50 to about 50,000 micrometers, more preferably from about 80 to about 1,000 micrometers, with a wall thickness from about 10 to about 1,000 micrometers, preferably from 20 to 500 micrometers. In the case of film, the film preferably possesses a thickness of from about 10 to about 1,000 micrometers, most preferably from about 25 to abut 500 micrometers. The film may be optionally supported by a permeable cloth or a screen.

Alternatively, the membrane is in the form of spirally round sheets.

The separation layer for the first separation stage membrane is optionally made of a copolymer or block polymer of the formula:

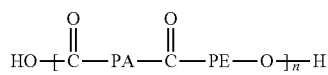

where PA is an aliphatic polyamide having 6 or 12 carbon atoms and PE is either poly(ethylene oxide) poly(tetramethylene oxide). These copolymers are commercially available as poly(ether-b-amide) multiblock copolymers from Arkema under the trade name of PEBAX®, and poly(butylene terephthalate) ethylene oxide copolymer available under the trade name of Polyactive®. Typically, the PEBAX polymers from Arkema include PEBAX 7233, PEBAX 7033, PEBAX 6333, PEBAX 2533, PEBAX 3533, PEBAX 1205, PEBAX 3000, PEBAX 1657, or PEBAX 1074. PEBAX 1657 exhibits a methane permeability of 5.12; see Barrer. H. Rabiee, et al., *J. Membrane Sci.* vol. 476, pp. 286-302 (2015).

Alternatively, the separation layer is made of repeating units of the following monomers, also known as Polyactive® multiblock copolymers:

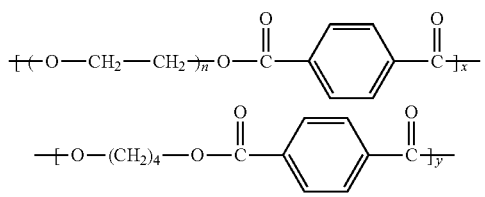

Alternatively, the separation layer of the first membrane stage is made of a copolymer or block polymer of tetramethylene oxide, and/or propylene oxide, or ethylene oxide. These copolymers or block polymers of tetramethylene oxide, and/or propylene oxide, or ethylene oxide may be conveniently synthesized, such as the polyester ether disclosed in U.S. Pat. No. 6,860,920, the polyester ethers of which are incorporated by reference;

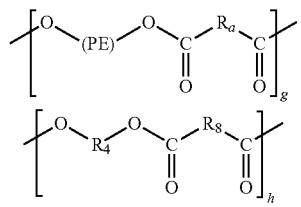

wherein PE may be one or more of the following structures:

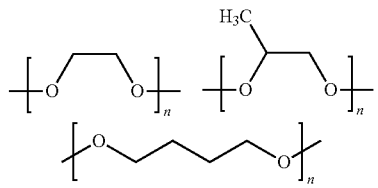

Other copolymers or block polymers of tetramethylene oxide, and/or propylene oxide, or ethylene oxide may be conveniently synthesized, such as polyimide ether disclosed in U.S. Pat. No. 5,776,990, the polyimide ethers of which are incorporated by reference.

The copolymers can be further obtained by copolymerization of acrylated monomers containing oligomeric propylene oxide, ethylene oxide, or tetramethyelene oxide.

Without being bound by any particularly theory, we believe that the rubbery membrane operates as follows: the product methane primarily remains on the retentate, high pressure side as a slow gas while water, $H_2S$, $CO_2$ and/or heavy hydrocarbons or VOC's are fast permeating gases that are permeated and removed at the low-pressure permeate side. The permeation of the impurities is due to their higher solubility in the polymeric separation layer, while $CH_4$ permeates at a slower speed than the impurities. Overall $H_2S$, $CO_2$, VOC's, siloxanes and water are "fast" gases while methane is a "slow" gas. Therefore, the rubbery membrane preferentially permeates water, $H_2S$, $CO_2$ and/or heavy hydrocarbons and VOC's from high pressure to low pressure, leaving behind at high pressure a lean product stream, enriched in methane, with less than about 0.1 wt. % of water. As a result, there is no need for recompression of the first retentate before it is fed to the second separation stage. Typically, the pressure drop between the feed gas and the retentate gas is less than 50 psi (3.45 bar), preferably less than 30 psi (2.07 bar), or more preferably less than 20 psi (1.38 bar).

Figure 3:
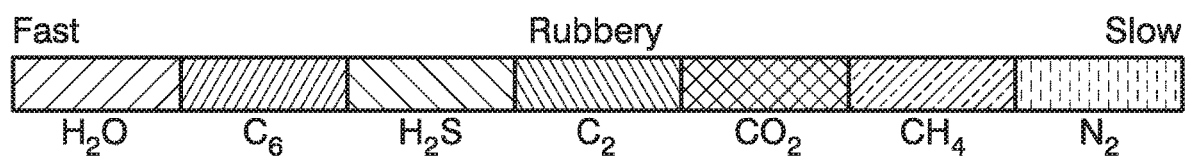
FIG. 3 illustrates relative permeation rates for a rubbery first separation stage membrane.

The membrane is robust and is operable with coalescing filters in condensing environments. The rubbery membrane fiber withstands exposure to VOC's such as benzene, toluene, and xylene (BTX), water, mercaptans or acid gases. An example of relative gas permeabilities for such a rubbery membrane is shown in FIG. 3.

Membranes of the Second Separation Stage

Figure 4:
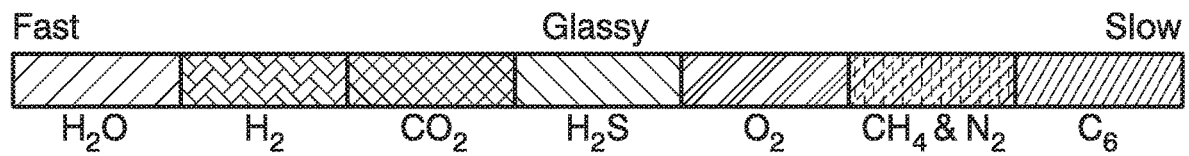
FIG. 4 illustrates relative permeation rates for a glassy second separation stage membrane.

These membranes are also known as "glassy" membranes. For the common glassy polymers, methane ($CH_4$) is a fairly slow gas, meaning it is not very permeable and substantially remains on the high pressure side (retentate) of the membrane, while $CO_2$ is a faster gas and, thus, more freely permeates from the high pressure to the low pressure side. Glassy membranes take advantage of the faster rate of $CO_2$ permeance to remove $CO_2$ from residual product gas. These membranes have a selectivity of at least 15, preferably at least 30, for $H_2S$ over $CH_4$. These membranes also have a selectivity of at least 20, preferably at least 35, for $CO_2$ over $CH_4$. A representation of the relative rates of permeation for glassy polymers is shown in FIG. 4.

It is noted that for the second stage glassy membrane, VOC's and siloxanes are slow gases and, thus, permeating slower than methane, such that they remain with the methane and only minimally permeate through the second stage, which is opposite of the first stage rubbery membrane where VOC's and siloxanes will permeate through the membrane.

Typically, the membrane of the second separation stage is made of cellulose acetate, a polysulfone, or a polyimide. The polyimide essentially consists of repeating units of dianhydride-derived units of formula (I) and diamine-derived units

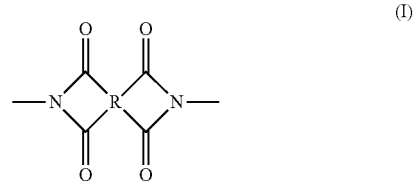

(I)

Each R is a molecular segment independently selected from the group consisting of formula (1), formula (2), formula (3), and formula (4):

(1)
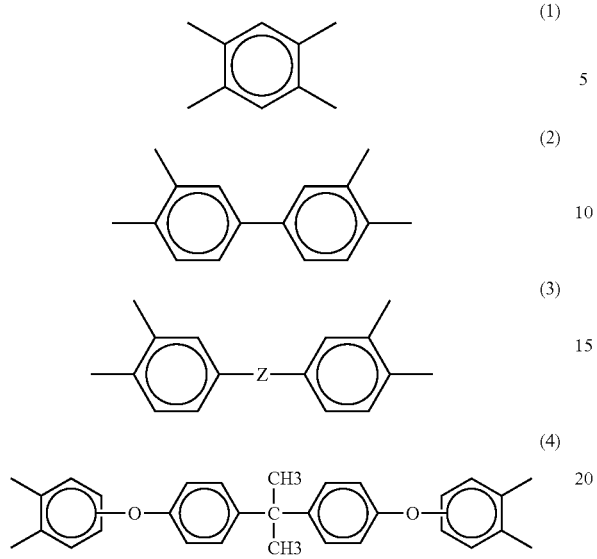
(2)

(3)

(4)

Each Z is a molecular segment independently selected from the group consisting of formula (5), formula (6), formula (7), formula (8), and formula (9).

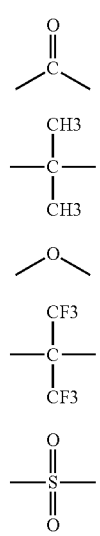

(5)

(6)

(7)

(8)

(9)

Each diamine-derived unit is a diamine-derived moiety independently selected from the group consisting of formula (A), formula (B), formula (C), formula (D), formula (E), formula (F), formula (G), and formula (H):

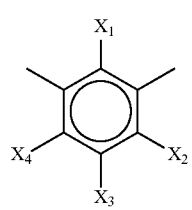

(A)

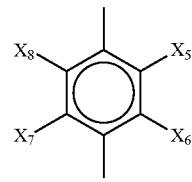 (B)

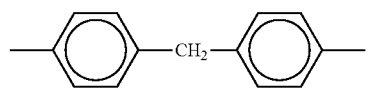 (C)

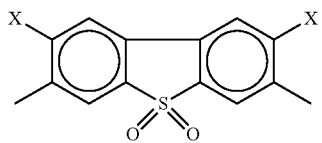 (D)

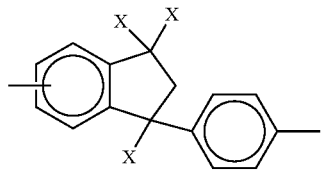 (E)

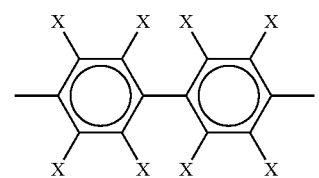 (F)

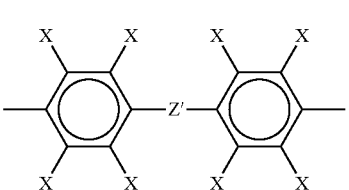 (G)

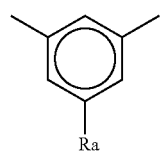 (H)

Each $X$, $X_1$, $X_2$, $X_3$, $X_4$, $X_5$, $X_6$, $X_7$, and $X_8$ is independently selected from the group consisting of hydrogen, an aromatic group, and a straight or branched $C_1$ to $C_6$ alkyl group. Each $R_a$ is a straight or branched $C_1$ to $C_6$ alkyl group having either a terminal hydroxyl group, a terminal carboxylic acid group, or a terminal carbon to carbon double bond. Each Z' is a molecular segment selected from the group consisting of formula (a), formula (b), formula (c), and formula (d):

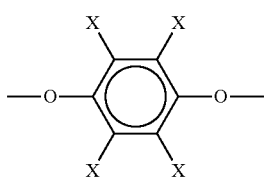 (a)

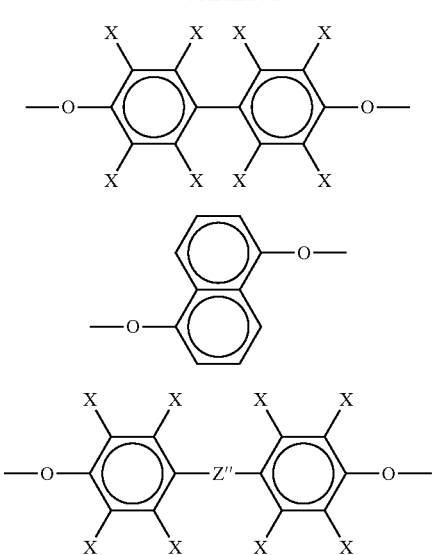

Each Z″ is a moiety selected from the group consisting of formula (U) and formula (V):

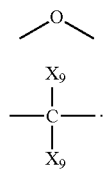

Each $X_9$ is selected from the group consisting of hydrogen, a straight or branched alkyl group having 1 to 6 carbon atoms, and a straight or branched pefluoroalkyl group having 1 to 6 carbon atoms.

Suitable membranes for the second gas separation membrane stage are commercially available from Medal®, a unit of Air Liquide Advanced Technologies, US.

Biomethane Production:

As illustrated in FIG. 1, a biogas or landfill gas feed 60 having about 5,000 ppm $H_2S$ at 100° F. is compressed in a main compressor 1 to a compressed feed 75, and a water removal apparatus 5 cools compressed feed 75 and separates water from the cooled feed 75 to produce a vapor phase stream 3. Stream 3 has a pressure of at least 100 psig, and is sent to a first separation stage of rubbery membranes 10, which permeates water and impurities such as $H_2S$ and $CO_2$ and VOCs to an output stream 20, having a low pressure of 2 psig, to be optionally rejected for flaring, or a controlled burning in a flaring system consists of a flare stack and pipes that feed the rejected gas to the stack.

The retentate from rubbery membrane 10 is sent as an output stream 15 to a second separation stage of glassy membranes 30, wherein a retentate output stream 35 is extracted as biomethane (product gas) having at least 94% methane, and containing 20 ppm or less of $H_2S$ at 190 psig. A permeate containing $CO_2$ and at least 40% $CH_4$ from the second separation stage of membranes 30 is withdrawn as output stream 25, which is and recycled back to compressor 1. Alternatively, the permeate 85 from the second stage is compressed in a second compressor 90, and the compressed permeate 95 is fed to the first separation stage.

Figure 2:
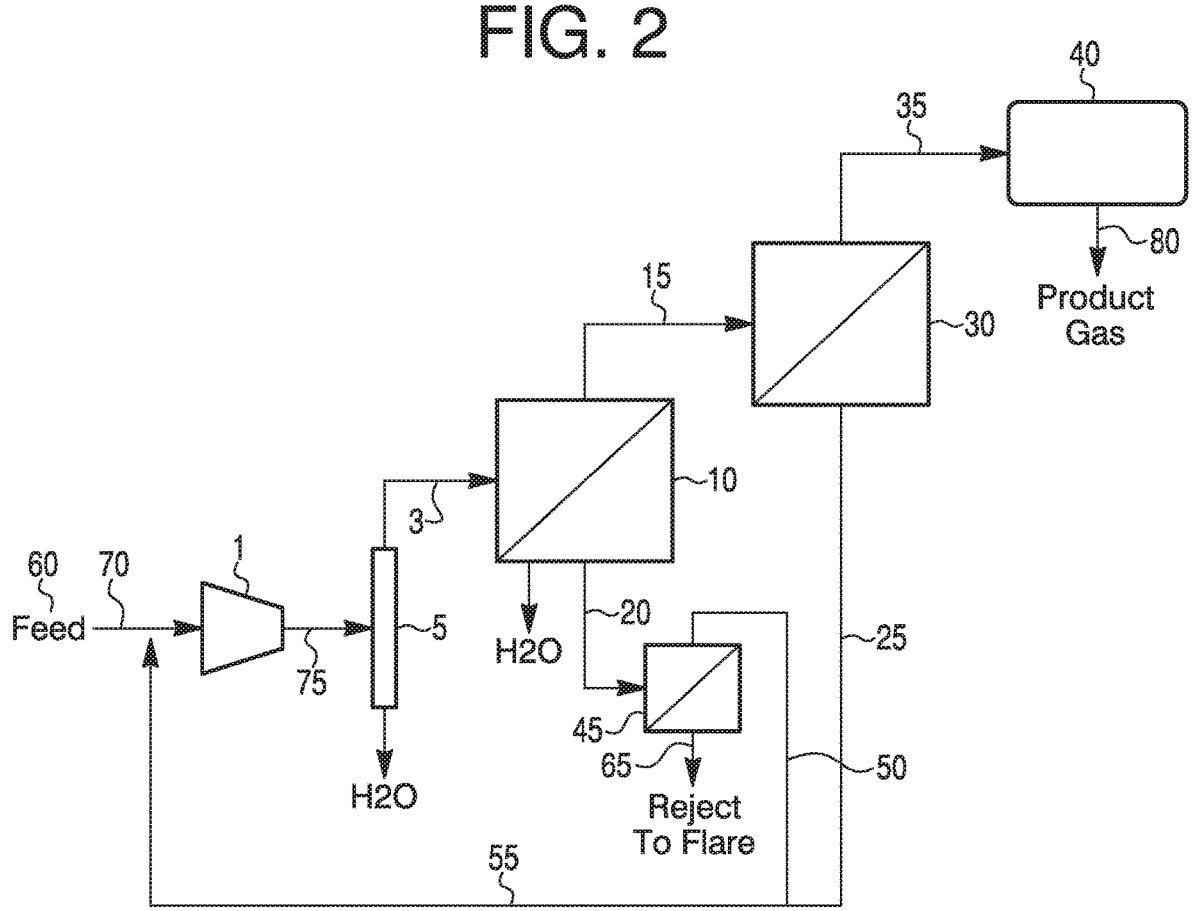
FIG. 2 illustrates a three-stage membrane system for biomethane production, and a $H_2S$ scavenger media.

Alternatively, as shown in FIG. 2, a $H_2S$ scavenger media 40 is used to process the retentate output stream 35 that may contain up to 100 ppm $H_2S$, and produce a product gas stream 80 (biomethane) from the scavenger media 40 having at least 94% methane, 4 ppm or less of $H_2S$, and less than or about 0.05 wt. % of water.

Alternatively, the $H_2S$ scavenger media 40 is located between first separation stage 10 and second separation stage 30 (not shown), to remove $H_2S$ prior to the retentate output stream 15 entering second separation stage of glassy membrane 30. Alternatively, a third separation stage containing rubbery or glassy membranes 45 (such as used in stage 1 or stage 2) is incorporated to process the permeate output stream 20, wherein a retentate output stream 50 is produced from the third stage 45. Output stream 50 is combined with the output stream 25 to form a recycle stream 55, which is then combined with feed 70 to be sent to compressor 1. The permeate from the third stage 45 is rejected as an output stream 65 at 2 psig to be flared.

PROPHETIC EXAMPLE

A raw biogas stream 60 has the following gas composition:
6.68% by volume water
1,000 ppm by volume $H_2S$
33.22% by volume $CO_2$
60% by volume $CH_4$ As shown in the process scheme of FIG. 1, the gas is compressed to 232 psia through a main compressor 1 and then fed into stage I, or first membrane stage 10, which contains a first separation stage of rubbery membranes exhibiting a selectivity for $H_2S$ over $CH_4$ of 31, and a selectivity for $CO_2$ over $CH_4$ of 4.6. The retentate output stream 15 from 10 is fed into a second membrane stage 30 containing glassy membrane exhibiting a selectivity for $H_2S$ over $CH_4$ of 35.5, and selectivity for $CO_2$ over $CH_4$ of 46.9. The permeate pressures for first membrane stage 10 is 41 psia, and for membrane stages 10 and 45, the permeate pressures are 15 psia. The total gas flow for the biomethane 35 or 80 is 0.54 MMSCFD ($CO_2$ concentration is below 2% by volume and $H_2S$ concentration is below 4 ppm). The material balance is shown in Table 1.

TABLE 1

|  | 60 | 70 | 3 | 20 | 15 | 35 or 80 | 25 |
|---|---|---|---|---|---|---|---|
| Vapour Fraction | 1.0000 | 1.00 | 1.0000 | 1.0000 | 1.0000 | 1.0000 | 1.0000 |
| Temperature (F.) | 100 | 100 | 100.0 | 100.0 | 91.7 | 81 | 91.7 |
| Pressure (psia) | 15 | 15 | 215 | 18 | 195 | 190 | 15 |
| Molar Flow (MMSCFD) | 1.00 | 1.905 | 184.7 | 0.4015 | 1.446 | 0.54 | 0.9052 |
| $CO_2$ | 0.3322 | 0.4135 | 0.4264 | 0.8271 | 0.6846 | <0.0200 | 0.5034 |
| $CH_4$ | 0.6000 | 0.5507 | 0.5679 | 0.1478 | 0.3152 | 0.98+ | 0.4962 |

TABLE 1-continued

|  | 60 | 70 | 3 | 20 | 15 | 35 or 80 | 25 |
|---|---|---|---|---|---|---|---|
| $H_2S$ | 0.0010 | 0.0007 | 0.0007 | 0.0025 | 0.0002 | 0.000004 | 0.0003 |
| $H_2O$ | 0.0668 | 0.0351 | 0.0049 | 0.0226 | 0.0001 | 0.000150 | 0.0001 |

The invention claimed is:

1. A method for producing biomethane, comprising:
compressing a biogas feed in a compressor to produce a compressed feed stream;
passing said compressed feed stream to a first separation stage comprising at least one polymeric gas separation membrane to retain a first gas mixture comprising at least 60% of methane, and to permeate a first low-quality gas mixture comprising impurities present in said biogas feed stream and less than 20% of methane, said biogas feed comprising 40-75% of methane, 20-55% of carbon dioxide, up to 5,000 ppm of hydrogen sulfide ("$H_2S$"), an amount of siloxanes, an amount of water, and up to 2,000 ppm of volatile organic compounds ("VOC's"), said at least one membrane of said first separation stage being selective for each of $H_2S$, siloxanes, and VOC's over $CH_4$,
sending a stream of said first gas mixture into a second separation stage comprising at least one polymeric gas separation membrane, to retain a second gas mixture containing at least 94% of methane, and to permeate a second permeate gas mixture comprising impurities present in said biogas feed stream and less than 70% of methane;
recycling a stream of said second permeate gas mixture to said compressor; and
withdrawing said second gas mixture from said second separation stage as biomethane, wherein said membrane of said first separation stage is substantially different from said membrane of said second separation stage, and said method excludes the use of regenerable adsorbent, said biomethane containing at least 94% methane, below 3% of $CO_2$, below 4 ppm of $H_2S$, below 100 ppm of VOC's, and below 0.01 wt. % of $H_2O$.

2. The method of claim 1, further comprising a step of passing said compressed feed stream to a water removal apparatus to remove water, after said step of compressing a biogas feed and prior to introducing said feed into said first separation stage.

3. The method of claim 1, wherein said compressed feed stream has a water content of less than 0.5 wt. %.

4. The method of claim 1, wherein said at least one membrane of said first separation stage is comprised of a porous polymeric substrate having at least one separation layer, wherein said substrate is selected from the group consisting of polyimides, poly sulfones, polyether ether ketones ("PEEK"), and mixtures thereof.

5. The method of claim 4, wherein said substrate is polyether ether ketones ("PEEK").

6. The method of claim 5, wherein said separation layer is made of a copolymer or block polymer of the formula:

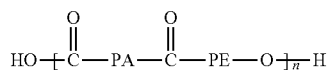

where PA is an aliphatic polyamide having 6 or 12 carbon atoms and PE is either poly(ethylene oxide) poly(tetramethylene oxide).

7. The method of claim 5, wherein said separation layer is made of repeating units of the following monomers:

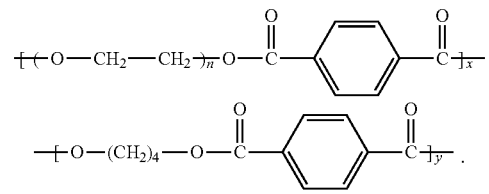

8. The method of claim 5, wherein said separation layer is made of a copolymer or block polymer of tetramethylene oxide, propylene oxide, and/or ethylene oxide.

9. The method of claim 1, wherein said at least one membrane of said first separation stage has a selectivity of at least 10 for $H_2S$ over $CH_4$.

10. The method of claim 1, wherein said stream of said first gas mixture has a pressure drop of less than 50 psi from said feed gas.

11. The method of claim 1, wherein said first gas mixture is comprised of at least 40% methane, at least 25% carbon dioxide, less than 1,000 ppm of hydrogen sulfide, less than 100 ppm of VOC's and siloxane, and less than 0.05 wt. % of water.

12. The method of claim 1, wherein said step of passing said compressed feed stream to a first separation stage further includes removing an amount of $H_2S$ from said first gas mixture using a $H_2S$ scavenger media to produce a low-$H_2S$ output stream having less than 4 ppm of $H_2S$ from said scavenger media, and sending said low-$H_2S$ output stream into said second separation stage polymeric membrane in said step of sending a stream of said first gas mixture into a second separation stage.

13. The method of claim 1, wherein said second separation stage has a selectivity of at least 20 for $CO_2$ over $CH_4$.

14. The method of claim 1, wherein said biomethane is comprised of at least 94% methane, below 3% of $CO_2$, below 4 ppm of $H_2S$, below 100 ppm of VOC's, and below 0.01 wt. % of $H_2O$.

15. The method of claim 1, wherein said second permeate gas mixture is comprised of about 30-70% methane, at least 30% $CO_2$, below 1,000 ppm of $H_2S$, below 100 ppm of VOC's, and below 0.05 wt. % of $H_2O$.

16. The method of claim 1, wherein said step of sending a stream of said first gas mixture into a second separation stage further includes sending said second gas mixture to a $H_2S$ scavenger media, to produce a low-$H_2S$ product stream having less than 4 ppm of $H_2S$ from said media.

17. The method of claim 1, wherein the permeate of said second stage is compressed in a second compressor, and said compressed gas is fed to said first stage.

18. The method of claim 1, wherein a selectivity of $H_2S$ over $CH_4$ of the polymeric gas separation membranes of the first separation stage is higher than that of the polymeric gas separation membranes of the second separation stage.

* * * * *